United States Patent [19]

Dayton et al.

[11] Patent Number: Plant 5,584

[45] Date of Patent: Dec. 3, 1985

[54] APPLE TREE

[75] Inventors: Daniel F. Dayton; Safi Korban, both of Urbana, Ill.; Edwin B. Williams, Lafayette, Ind.; Jules Janick; Frank H. Emerson, both of W. Lafayette, Ind.; L. Fredric Hough, Blairstown, N.J.

[73] Assignee: Purdue Research Foundation, West Lafayette, Ind.

[21] Appl. No.: 572,809

[22] Filed: Jan. 23, 1984

[51] Int. Cl.[4] ..... A01H 5/03

[52] U.S. Cl. ..... Plt./34

[58] Field of Search ..... Plt./34

[56] References Cited

PUBLICATIONS

Bulletin Entitled "Co-op 19, 20, 21, and 22: Four Scab-Resistant Apple Selections Released For Advanced Testing" (Bulletin 755).

*Primary Examiner*—Robert E. Bagwill

*Attorney, Agent, or Firm*—Barnes & Thornburg

[57] ABSTRACT

A new and distinct cultivar of apple tree is distinctly characterized by its high fruit quality, the attractive red color and good flavor of the fruit, and its resistance to *Venturia inaequalis* (Cke.) Wint., the causal agent of apple scab disease. This new cultivar of apple tree, now designated as COOP 21, is a seedling of known parentage planted in 1969 in the PA block of the apple breeding orchard at the Pomology Research Center at the Illinois Agricultural Experimental Station, Urbana, Ill., which site is a cultivated area. In the above-mentioned orchard, its position was Row 1, Tree 58, having the designation PRI 2259-100 in the breeding records. After observation, the selection was asexually reproduced by grafting on both seedlings and dwarfing roots. The grafted material has maintained the described characteristics after propagation.

1 Drawing Figure

DESCRIPTION OF THE DRAWINGS

FIG. 1 is a photograph showing typical examples of fruit and foliage of COOP 21.

BACKGROUND OF THE INVENTION

The present new cultivar is a seedling produced from crossing the seedling N.J. 123249 as the seed parent and the seedling PRI 1235-100 as the pollen parent in 1966 at New Brunswick, N.J. This new cultivar carries a genetic factor, $V_f$, inherited from *Malus floribunda* 821, which causes it to be resistant to infection caused by *Venturia inaequalis*. The presence of this factor has been proven repeatedly by controlled inoculation tests in the Purdue University greenhouse of the seedling and its offspring produced from controlled crosses. A complete pedigree is shown below:

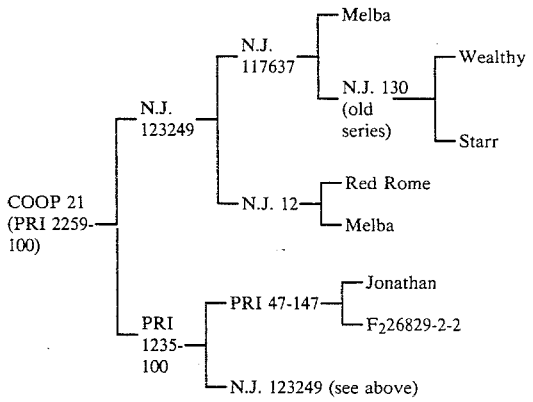

$F_2$26829-2-2 has the following parentage:

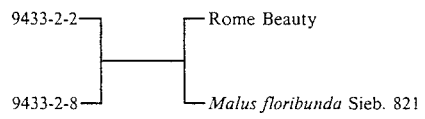

The new cultivar produces a moderately upright and vigorous tree similar to 'Delicious'. It is field immune to apple scab and is only slightly susceptible to fireblight and powdery mildew.

The apple fruit has fine dessert and culinary quality quite similar to 'Prima', but is less acidic. Additionally, a higher proportion of the fruit surface has a bright red color. The characteristic texture and flavor are maintained up to four weeks at 34° F. The skin of the fruit is smooth and very glossy, having light tan dots spaced widely, but being more numerous near the apex. The skin is moderately tough.

DETAILED DESCRIPTION OF THE NEW CULTIVAR

The following is a detailed description of this new cultivar with color designations according to the 1966 Royal Horticultural Society Colour Chart, issued by The Royal Horticultural Society of London.

FLOWER

Pedicel: (Length) 1.7–2.1 cm.

Corolla: (Diameter) 3.7–4.0 cm fully expanded.

Color: (Bud) Pink, plate 52C. (Open) Pale pink, plate 56D.

FRUIT

Shape: Roundish to slightly oblate.

Size: (Axial diameter) 6.5 cm; (Transverse diameter) 7.4 cm.

Color: Bright medium red (plates 46C to 46B,) covering up to 90% of the fruit surface.

Skin: Smooth and very glossy; light tan dots widely spaced, but numerous near apex; thin, moderately tough.

Stem: 1.8–2.1 cm in length; medium thickness and medium stiffness.

Cavity: Acute, deep, medium width, russeted.

Basin: Medium depth and width, with lobes on inner sloping sides.

Calyx: Persistent, convergent, partly to fully closed.

Calyx tube: Vase-shaped.

Stamens: Median.

Core lines: Meeting.

Core: Median, closed, small.

Carpels: Mucronate, elongated, not tufted.

Seeds: Acute, not tufted.

Flesh:

*Texture.*—Fine-grained, firm, crisp.

*Color.*—Pale yellow (Plate 11D).

*Quality.*—Very good, sub-acid to mild flavor; resembles 'Prima' but less acidic.

Maturity season: With 'Prima'.

Storage characteristics: Retains excellent texture and flavor up to four weeks at 34° F.

Use: Very good dessert and culinary apple.

TREE AND FOLIAGE

Growth habit: Moderately upright and vigorous.

Foliage: Ovate with single serrate margin, glabrous, not rugose, apex acuminate, base obtuse, length to width ratio 1.5:1.

Disease resistance: Resistant to scab, only slightly susceptible to fireblight and powdery mildew.

What is claimed is:

1. A new and distinct apple tree substantially as shown and described, particularly characterized by resistance to apple scab, attractive red color, good flavor, and maturing approximately with 'Prima', and four weeks before 'Jonathan'.

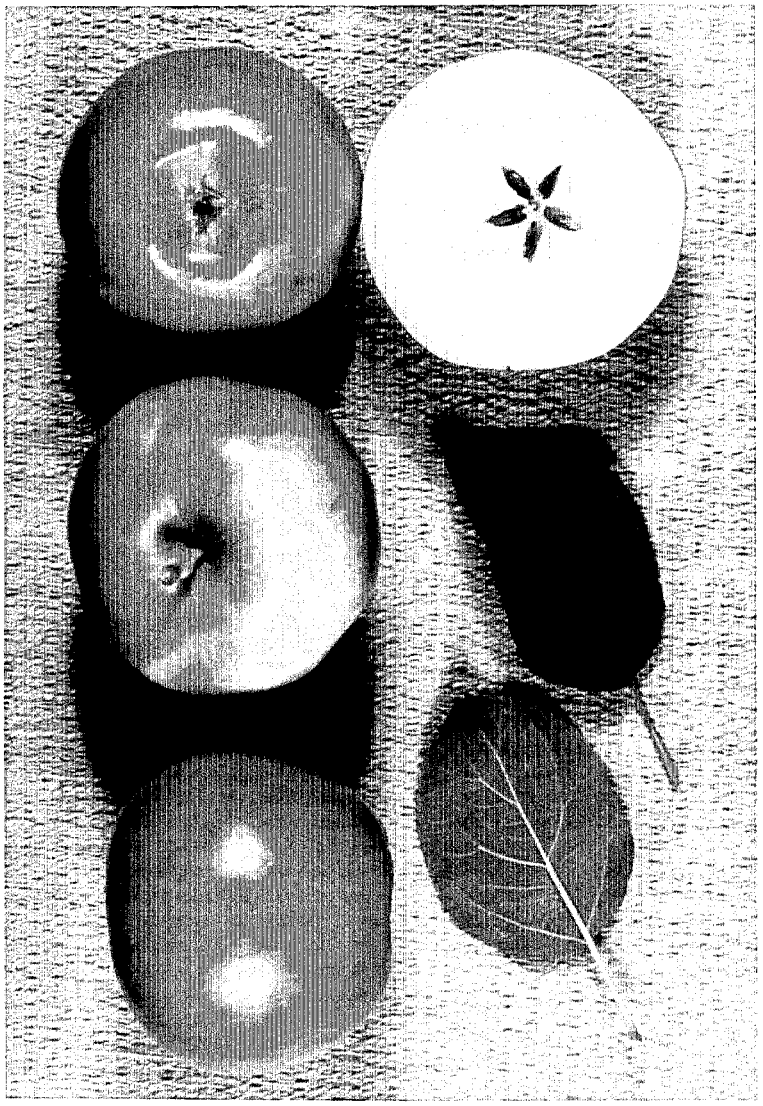

* * * * *